(12) United States Patent
Okuyama

(10) Patent No.: US 8,605,984 B2
(45) Date of Patent: Dec. 10, 2013

(54) CIGARETTE INSPECTION DEVICE

(75) Inventor: Tetsuya Okuyama, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 13/480,638

(22) Filed: May 25, 2012

(65) Prior Publication Data
US 2012/0230578 A1 Sep. 13, 2012

Related U.S. Application Data

(63) Continuation of application No. PCT/JP2009/069912, filed on Nov. 26, 2009.

(51) Int. Cl.
*G06K 9/00* (2006.01)
(52) U.S. Cl.
USPC .......................... 382/143; 382/141
(58) Field of Classification Search
CPC ........................................ G06T 7/001
USPC ....................... 382/141, 143, 151
See application file for complete search history.

(56) References Cited

U.S. PATENT DOCUMENTS

| | | | | |
|---|---|---|---|---|
| 5,353,357 | A * | 10/1994 | Longest et al. | 382/141 |
| 5,588,068 | A * | 12/1996 | Longest et al. | 382/141 |
| 5,979,140 | A | 11/1999 | Focke et al. | |
| 7,779,846 | B2 | 8/2010 | Spatafora et al. | |
| 2004/0173226 | A1 * | 9/2004 | Hanaoka et al. | 131/280 |
| 2006/0050267 | A1 | 3/2006 | Murakami et al. | |

FOREIGN PATENT DOCUMENTS

| | | |
|---|---|---|
| JP | 2002-99898 A | 4/2002 |
| JP | 2003-153679 A | 5/2003 |
| JP | 3437753 B2 | 8/2003 |
| JP | 2006-174835 A | 7/2006 |
| JP | 2007-184589 A | 7/2007 |

\* cited by examiner

*Primary Examiner* — Edward Park
(74) *Attorney, Agent, or Firm* — Birch, Stewart, Kolasch & Birch, LLP

(57) ABSTRACT

A cigarette inspection device for inspecting a filter quality through an inspection image of filter end faces in a bundle of cigarettes for accurately detecting, for example, only contaminations. A pattern image is used for detecting a cigarette location on the basis of a preset location of each cigarette in the cigarette bundle and a search area on the inspection image is set. The pattern image is shifted within the search area, thereby obtaining a position at which the pattern image coincides with an image of the filter end face. An image of a filter end face of the cigarette is cut out from the inspection image according to the detected position, and quality (contamination) is inspected. Inspection results obtained with respect to the cigarettes are aggregated, and a judgment is made on the quality (presence or absence of a contamination) of the filter end face.

11 Claims, 7 Drawing Sheets

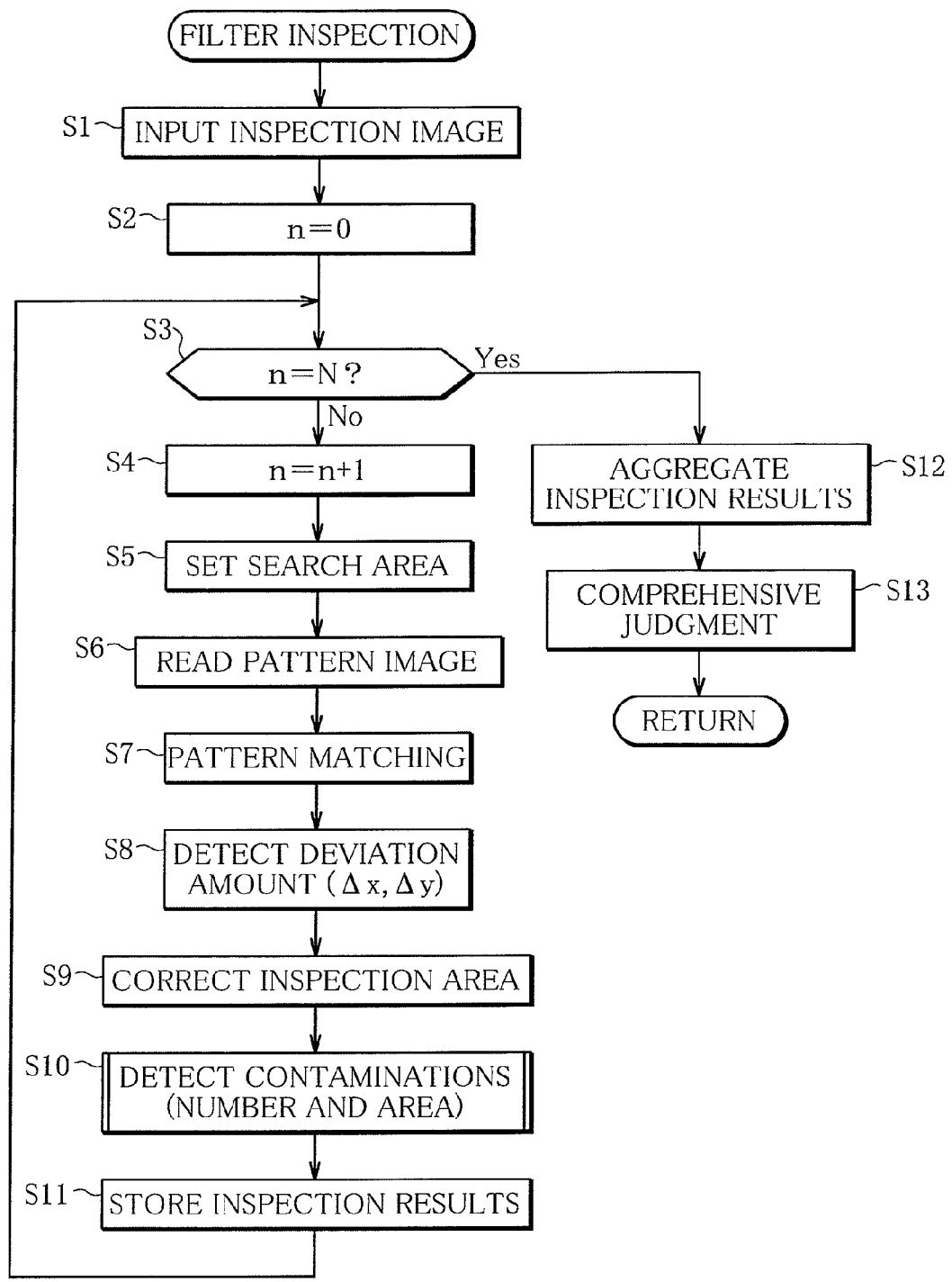

CIGARETTE INSPECTION DEVICE

CROSS-REFERENCE TO RELATED APPLICATIONS

This application is a Continuation of co-pending PCT International Application No. PCT/JP2009/069912 filed on Nov. 26, 2009, which designated the United States. The entire content of the above application is hereby incorporated by reference into the present application.

TECHNICAL FIELD

The present invention relates to a cigarette inspection device being capable of accurately detecting a contamination in the filter of a filter cigarette.

BACKGROUND ART

Filter cigarettes are wrapped in bundles each containing a predetermined number of (twenty, for example) cigarettes by a wrapping machine as disclosed in Patent Document 1, and are thus produced into tobacco packs. The wrapping machine disclosed in Patent Document 1 wraps a wrapping material around the periphery of a bundle of filter cigarettes arranged in the same orientation in multiple tiers. The wrapping machine then folds both the open ends of the wrapping material in the inward direction to close the ends, thereby wrapping the bundle of cigarettes.

PRIOR ART DOCUMENT

Patent Document

Patent Document 1: U.S. Pat. No. 3,437,753

SUMMARY OF THE INVENTION

Problem to be Solved by the Invention

In rare cases, machine oil used in various machines in a cigarette manufacturing process adheres to a filter end face of the cigarettes to be wrapped as mentioned. The cigarettes contaminated in their filter end face must be removed (eliminated) from an object of wrapping in order to ensure the quality of tobacco pack. In conventional art, for example, the filter end faces of a bundle of cigarettes supplied to a wrapping machine is imaged, and the image is processed, to thereby inspect the quality of cigarettes, or more specifically, the presence or absence of a contamination.

A conventional image processing, however, simply discriminates the color components of inspection images. It is then difficult to distinguish, for example, between a contamination of a filter end face and a tobacco shred that is merely attached on the filter end face. For that reason, normal products merely attached with tobacco shreds on their filter end faces are occasionally eliminated for being recognized as contaminated. When the array of cigarettes supplied to the wrapping machine is disturbed and collapse, gaps produced between the cigarettes due to the disturbance of array and found in the image of the filter end faces are sometimes detected as contaminations in error.

The present invention has been made to solve the foregoing problem. It is an object of the present invention to provide a cigarette inspection device being capable of inspecting a filter quality through an inspection image of filter end faces of a bundle of cigarettes and accurately detecting, for example, only contaminations, even if there is a disturbance in the array of the cigarettes to be supplied to and wrapped by a wrapping machine.

Means for Solving the Problem

In order to achieve the above object, the present invention relates to a cigarette inspection device for imaging filter end faces in a cigarette bundle containing a predetermined number of filter cigarettes horizontally arranged when wrapping process of the cigarette bundle is unfinished, analyzing an inspection image in which the filter end faces are imaged, and inspecting quality of the filter end faces.

The cigarette inspection device comprises cigarette-location detecting means for determining a pattern image to be used for detecting a cigarette location on the basis of a preset location of each cigarette in the cigarette bundle, setting a search area with respect to each cigarette's location on the inspection image for detecting the cigarette location by the use of the pattern image, moving the pattern image obtained on the basis of a cigarette location in the cigarette bundle within the search area that is determined with respect to each cigarette's location on the inspection image, and obtaining an image position at which the pattern image coincides with an image of the filter end face of the cigarette; and quality inspection means for cutting out the image of the filter end face of the cigarette from the inspection image according to the detected image position of the cigarette, and inspecting the quality of the filter end face of the cigarette.

Preferably, the cigarette inspection device further comprises quality judging means for aggregating results of contamination inspection, which are obtained with respect to cigarette locations in the cigarette bundle, and obtaining a result of contamination judgment on the cigarette bundle.

The pattern image is prepared as a partial image, in which a part of the filter end face of each of leftmost, rightmost, upper and lower cigarettes in the cigarette bundle is cut out in an arc-like shape against a background of an outer side of the cigarette bundle. The pattern image is then stored in a pattern image memory.

The cigarette-location detecting means is configured to find out a cigarette location in the inspection image as an amount of deviation ($\Delta x$, $\Delta y$) of the position of the pattern image from a reference location that is preset within the search area when the pattern image coincides with the image of the filter end face of the cigarette,.

The quality inspection means is configured, for example, to find out a number of contaminations and/or area of contaminated regions in the filter end face. The quality judging means judges that the cigarette bundle is defective when the number of contaminations or the area of contaminated regions in the filter end face exceeds a preset first threshold value or when the total number of contaminated regions or the total area of the contaminated regions in the filter end faces of cigarettes in the bundle exceeds a preset second threshold value.

Preferably, the inspection image is obtained by imaging the filter end faces of the cigarette bundle before a filter-side end of the cigarette bundle is closed with a wrapping material in a wrapping machine.

Technical Advantages of the Invention

According to the cigarette inspection device of the present invention, regardless of a disturbance in the cigarette bundle, a location of each cigarette can be detected in the inspection image by comparing the pattern image prepared on the basis of the cigarette location in the cigarette bundle and the image of the filter end face. Therefore, the image of the filter end face of each cigarette can be accurately cut out for quality inspection. It is therefore possible to accurately detect, for example, contaminations of filter end faces in the cigarette bundle, regardless of a disturbance in array of cigarettes in the bundle.

Location of each cigarette can be easily detected because the search area is set in the inspection image in accordance with the pattern image on the basis of the location of each cigarette. If there is an absence of image of a filter end face, which coincides with the pattern image in the search area, it can be recognized that the corresponding cigarette is missing (omitted) from the cigarette bundle or detected as shape abnormality. Not only the contaminations of the filter end faces but also abnormality in the cigarette bundle can be inspected at the same time.

In the quality inspection, the number of contaminations and/or the area of contaminated regions in the filter end face of each cigarette is obtained, and the total of results of the inspection on each cigarette of the cigarette bundle is also obtained, to thereby evaluate the above factors in a comprehensive manner. Consequently, even if the contamination level (the number of contaminations and/or the area of contaminated regions) of each cigarette is minor, it is possible to accurately detect a cigarette bundle that is much contaminated in filters as a whole.

BRIEF DESCRIPTION OF THE DRAWINGS

FIG. 7 shows an example of an image inspection routine that is conducted by the cigarette inspection device of the present invention.

BEST MODE FOR CARRYING OUT THE INVENTION

A cigarette inspection device of the present invention will be described below in detail with reference to the drawings.

The cigarette inspection device images the filter end faces of a predetermined number of filter cigarettes that are horizontally arranged and to be supplied to and wrapped by a wrapping machine before the filter cigarettes are wrapped the wrapping machine, analyzes an inspection image that has been taken including the filter end faces, and thus inspects the quality of the filter end faces, or more specifically, the presence or absence of contaminations of the filter end faces.

Figure 1:
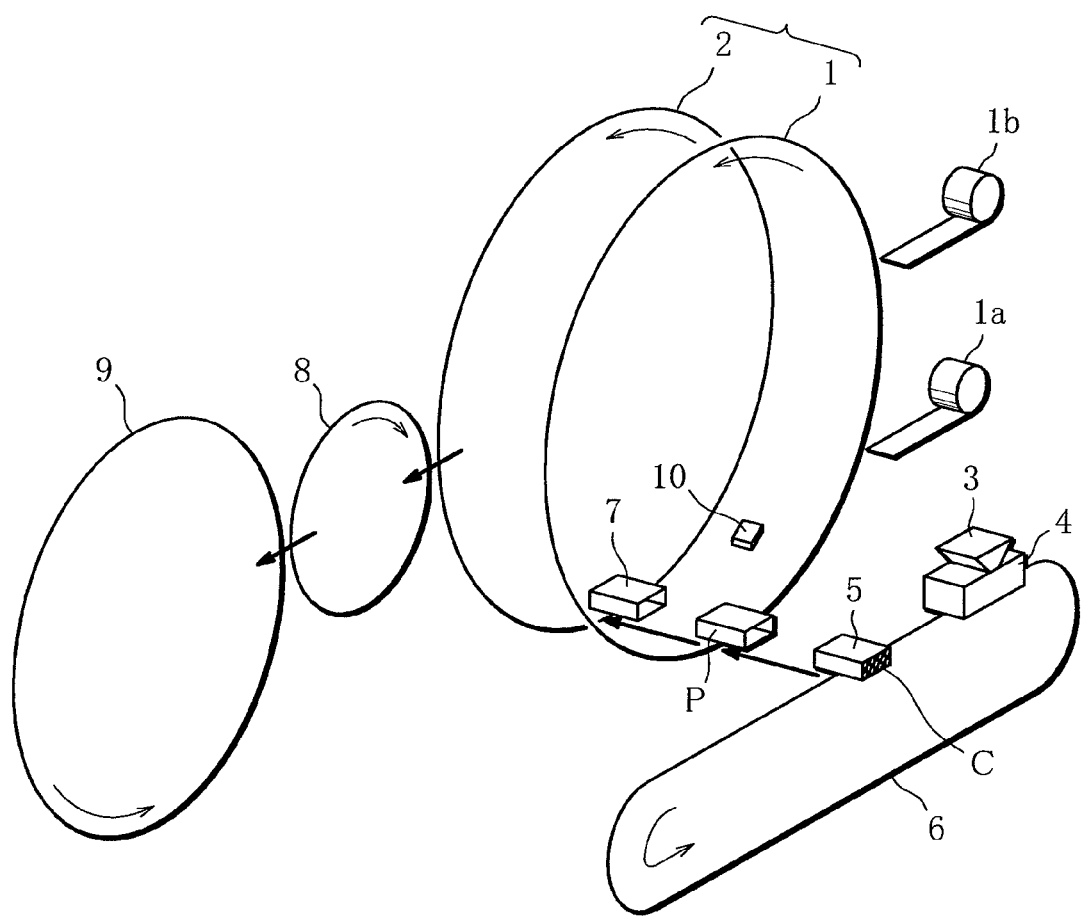
FIG. 1 is a schematic configuration view of a tobacco-pack wrapping machine in which a cigarette inspection device of the present invention is installed.

The cigarette wrapping machine in which the cigarette inspection device of the present invention is installed is fully described in Patent Document 1, for example. The wrapping machine comprises a wrapping turret 1 for forming a predetermined wrapping material into a shape of a bottomed rectangular tube as schematically shown in FIG. 1; and a closing turret 2 disposed next to and concentrically with the wrapping turret 1. The closing turret 2 receives a bundle of a plurality of (twenty, for example) cigarettes previously horizontally arranged in the inside of the bottomed rectangular tube-shaped wrapping material that has been formed by the wrapping turret 1, and folds an open end portion of the tube-shaped wrapping material to close the tube-shaped wrapping material.

Figure 2:
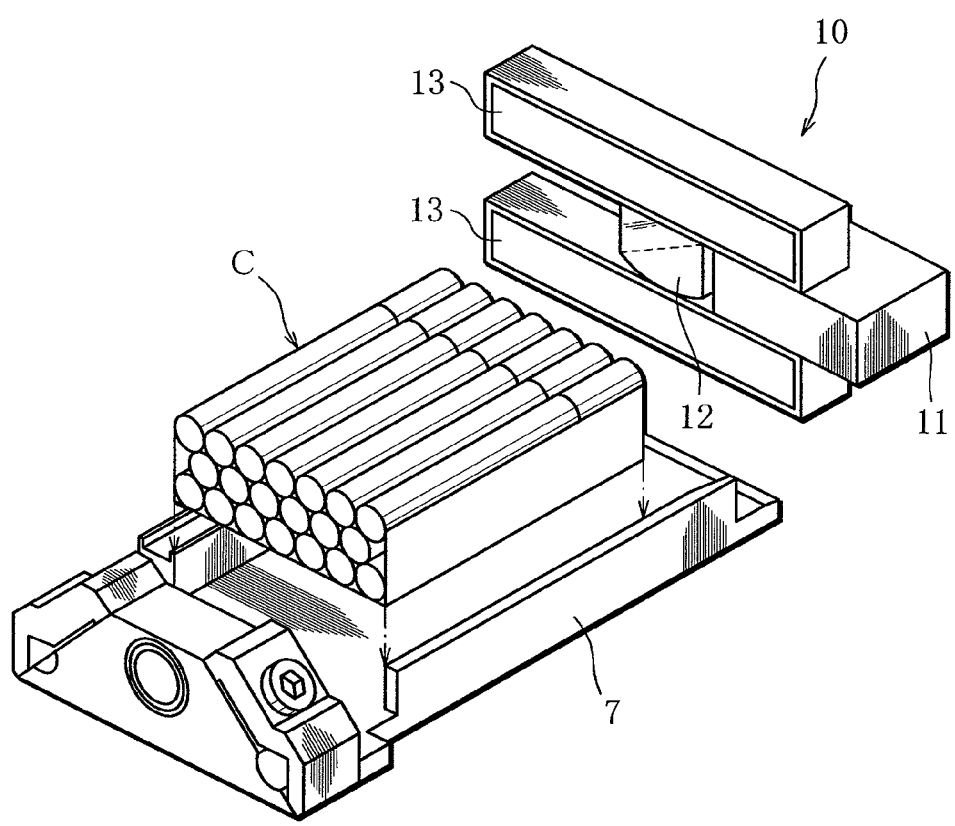
FIG. 2 shows a bundle of filter cigarettes supplied to the tobacco-pack wrapping machine and a relationship between the bundle and a camera for imaging the filter end faces of the bundle.

The cigarette bundle is formed by an arrangement machine 4. The arrangement machine stacks filter cigarettes supplied to a hopper 3 with filters thereof arranged in the same orientation, in three tiers of seven, six, and seven. The cigarette bundle is then placed into a carrying pocket 5 and delivered to the wrapping turret 1 by means of a chain conveyer 6. The cigarette bundle C is pushed out of the carrying pocket 5 by a plunger, not shown, and is placed inside a wrapping material P having the shape of a bottomed rectangular tube, which has been formed in the wrapping turret 1. In this state, the cigarette bundle C is transferred with the bottomed rectangular tube-shaped wrapping material P into a mandrel 7, for example, as shown in FIG. 2, of the closing turret 2.

The closing turret 2 rotates to move the mandrel 7 along a circumferential direction of the closing turret 2 and inwardly folds the open end portion of the bottomed rectangular tube-shaped wrapping material P that contains the cigarette bundle C, thereby closing the tube-shaped wrapping material P and wrapping the cigarette bundle C. A tobacco pack formed by wrapping the cigarette bundle C is directed from the closing turret 2 through a transfer turret 8 to a drying turret 9. The tobacco pack is subjected to a drying treatment in the drying turret 9 and then discharged as a product.

Reference marks 1a and 1b in FIG. 1 represent wrapping-material suppliers that are disposed along a circling orbit of the wrapping turret 1 and supply to a wrapping mandrel of the turret 1 an inner wrapping material Pa made of an aluminum vapor-deposition sheet or the like and an outer wrapping material Pb made of a paper sheet or the like. The inner wrapping material Pa and the outer wrapping material Pb are superposed on each other and wound around the wrapping mandrel, thereby forming the bottomed rectangular tube-shaped wrapping material P.

With respect to the cigarette wrapping machine thus configured, basically, a camera 10 for imaging the filter end faces of the cigarette bundle C in the cigarette inspection device of the present invention is disposed alongside a circling orbit of the closing turret 2. Particularly, the camera 10 is disposed slightly downstream from a position at which the mandrel 7 receives the cigarette bundle C with the wrapping material P, and images the filter end faces of the cigarette bundle C before the open end portion of the wrapping material P is folded in the inward direction.

As shown in FIG. 2, for example, the camera 10 is a thin camera of a so-called side-view type, which takes an image in a lateral direction of a camera body 11 by use of an optical system 12, such as a prism, which is mounted on a lateral side of the camera body 11. Strobes 13 for illuminating an object to be imaged are disposed above and below the camera body 11. The strobes 13 are of a compact type using, for example, LED as an illuminant. Since the camera 10 is of a compact type, it is possible to place the camera 10 in a space between the wrapping turret 11 and the closing turret 2. The filter end faces of the cigarette bundle C supplied to the mandrel 7 of the closing turret 2 are imaged by the camera 10 before being closed with the wrapping paper P.

Figure 3:
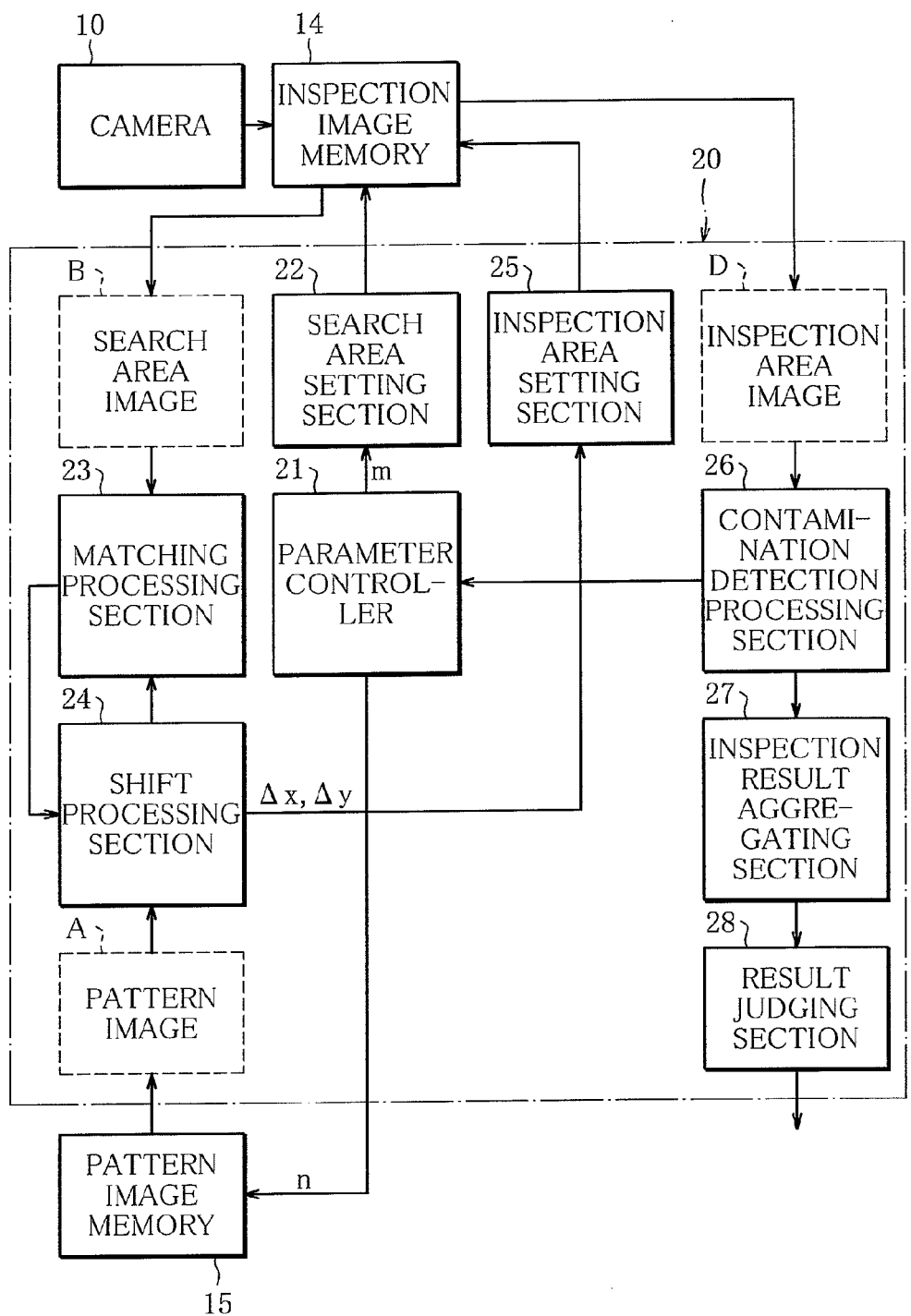
FIG. 3 is a schematic configuration view of the cigarette inspection device of the present invention.

FIG. 3 is a schematic configuration view of the cigarette inspection device of the present invention. The cigarette inspection device has an inspection image memory 14 for storing an inspection image which is taken by the camera 10 and includes the filter end faces of the cigarette bundle C, and an image processor 20 for analyzing the inspection image (image of the filter end faces of the cigarette bundle C) which is stored in the inspection image memory 14. The image processor 20 includes a microprocessor for analyzing the inspection image, for example, according to a preloaded program. In the inspection image of the cigarette bundle C taken by the camera 10, the filter end face of each cigarette illuminated by the strobes 13 is found as a bright image zone, whereas a gap between cigarettes and the lateral portions of cigarettes are found as dark image zones as they do not reflect illuminating light.

As described below, the image processor 20 detects the location of each cigarette (location of each filter end face) in the inspection image by the use of the pattern images which are prepared and saved in the pattern image memory 15, and then selectively cuts out the image of the filter end face at each detected location to inspect the presence and absence of a contamination, the size of the contamination, etc.

Figure 4:
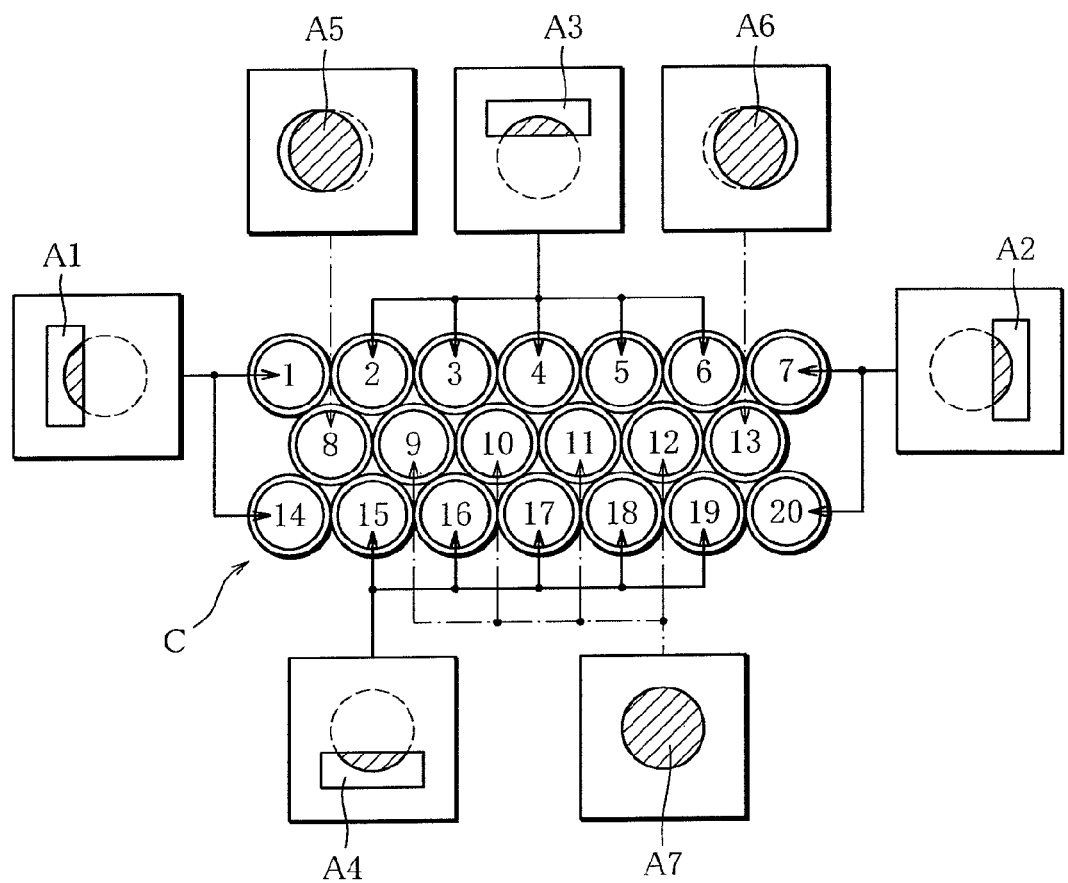
FIG. 4 shows a concept of image inspection conducted by the cigarette inspection device of the present invention.

The pattern images are determined by the locations of the cigarettes forming the cigarette bundle C. When the cigarette bundle C is formed of twenty cigarettes, the pattern images are determined, for example, as shown in FIG. 4.

Two leftmost cigarettes [1] and [14] among twenty cigarettes [1] to [20] stacked in three tiers of seven, six, and seven do not have any adjacent cigarettes on their left side. In this case, a pattern image A1 is determined for these cigarettes [1] and [14]. The pattern image A1 corresponds to a left-side area of the filter end face of each of these two cigarettes, the left-side area being vertically cut out in a strip-like shape from the filter end face. An arc-like image portion in the pattern image A1 is defined as a cigarette zone (filter zone), and the rest (left side portion) as a background (dark portion). Likewise, two rightmost cigarettes [7] and [20] do not have any adjacent cigarettes on their right side, and a pattern image A2 is determined for these cigarettes [7] and [20]. The pattern image A2 corresponds to a right-side area of the filter end face of each of these two cigarettes [7] and [20], the right-side area being vertically cut out in a strip-like shape. An arc-like image portion in the pattern image A2 is defined as a cigarette zone, and the rest (right side portion) as a background (dark portion).

As to the cigarettes in the top tier, except for the leftmost and rightmost ones, that is, five cigarettes [2], [3], [4], [5] and [6], there are no adjacent cigarettes above them. Therefore, a pattern image A3 is determined for these cigarettes [2], [3], [4], [5] and [6]. The pattern image A3 corresponds to an upper-side area of the filter end face of each of these five cigarettes [2], [3], [4], [5] and [6], the upper-side area being cut out sideways in a strip-like shape. An arc-like image portion in the pattern image A3 is defined as a cigarette zone, and the rest (upper portion) as a background. As to the cigarettes in the bottom tier, except for the leftmost and rightmost ones, that is, five cigarettes [14], [15], [16], [17] and [18], there are no adjacent cigarettes below them. In this case, a pattern image A4 is determined for these cigarettes [14], [15], [16], [17] and [18]. The pattern image A4 corresponds to a lower-side area of the filter end face of each of these five cigarettes [14], [15], [16], [17] and [18], the lower-side area being cut out sideways in a strip-like shape. An arc-like image portion in the patter image A4 is defined as a cigarette zone, and the rest (lower portion) as a background.

The cigarettes [8] to [13] in the middle tier have adjacent cigarettes above and below them. A pattern image A5 is determined for the leftmost cigarette [8]. The pattern image A5 corresponds to a circular area which is eccentrically cut out the filter end face of the cigarette [8] with the center of the pattern image A5 displaced to left. An oval image portion in the pattern image A5 is defined as a cigarette zone (filter zone), and the rest (left side portion) as a background. In a similar manner, a pattern image A6 is determined for the rightmost cigarette [13], which is a circular area eccentrically cut out the filter end face of the cigarette [13] with the center of the pattern image A6 displaced to right. An oval image portion in the image pattern A6 is defined as a cigarette zone (filter zone), and the rest (right side portion) as a background.

As to four cigarettes [9], [10], [11] and [12] located at the center and each having adjacent cigarettes on its right, left, above and below, a pattern image A7 is determined for these cigarettes [9], [10], [11] and [12]. The pattern image A7 corresponds to a circular area which is concentrically cut out the filter end face of each of the cigarettes [9], [10], [11] and [12]. A circular image portion in the pattern image A7 is defined as a cigarette zone (filter zone).

The pattern images for detecting the location of each cigarette (location of each filter end face) in the inspection image are prepared as the pattern images A1 to A7 reflecting the locations of the respective cigarettes, and are stored in the pattern image memory 15.

The image processor 20 will be briefly described below. The image processor 20 includes a parameter controller 21 which controls a control parameter n for individually inspecting contamination in the filter end face of each of the cigarettes forming the cigarette bundle C. The control parameter n specifies the location of each cigarette in the cigarette bundle C, and a maximum value thereof is set as the number N of cigarettes forming the cigarette bundle C. The control parameter n is sequentially incremented from [n=1] to [n=N]. The cigarette at the location specified by the control parameter n is subjected to a contamination inspection.

More specifically, when the control parameter n is specified by the parameter controller 21, the pattern image A (A1 to A7) that is prepared for the location of each cigarette is selectively read out from the pattern image memory 15 according to the control parameter n. A search area setting section 22 specifies the location of a cigarette to be inspected according to the control parameter n, and determines a search area S of the inspection image stored in the inspection image memory 14. In other words, the search area S of the inspection image is determined with respect to the location of each cigarette as mentioned later, and the search area S in the inspection image memory 14 is determined by the control parameter n.

A matching processing section 23 receives through a shift processing section 24 a pattern image A that has been selectively read out from the pattern image memory 15 according to the control parameter n. The matching processing section 23 functions to find out an image portion with which the pattern image A coincides within the search area S specified by the control parameter n in the inspection image and a location of the image portion in cooperation with the shift processing section 24.

The shift processing section 24 contributes to a comparison between the pattern image A and an image B in the search area S. The comparison is conducted by the matching processing section 23, while shifting the pattern image A over the search area S. When detecting the image portion that coincides with the pattern image A within the image B of the search area S, the matching processing section 23 determines shift amount Ax, Ay by which the pattern image A is shifted from a predetermined initial location by the shift processing section 24.

The matching processing section 23 detects a location on the search area S, which is indicated by the shift amount $\Delta x$, $\Delta y$, as a cigarette location.

Figure 5:
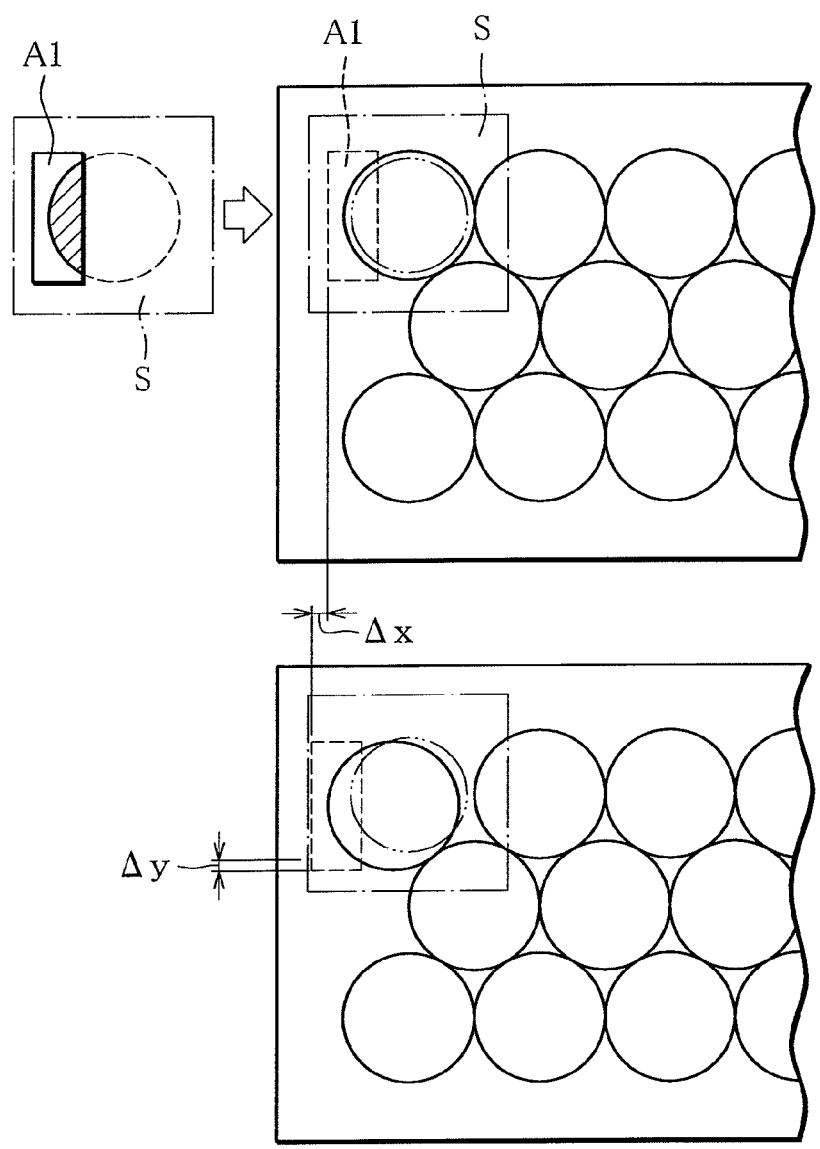
FIG. 5 shows a relationship between a pattern image and a search area in an inspection image, and a concept of cigarette location detection.

More specifically, for example, when the upper left cigarette [1] in the cigarette bundle C is specified by the control parameter n, the pattern image A1, in which an image of a left-side arc-like portion of the filter end face of the cigarette [1] is cut out, is selected from the pattern image memory 15 as shown in FIG. 5. The search area S of which the center is located at the proper location of the upper left cigarette [1] is determined in the inspection image as shown in FIG. 5. The search area S has a rectangular shape, for example.

A comparison reference position of the pattern image A1 with respect to the search area S that is set as described above is determined as a position at which the pattern image A1 coincides with the inspection image (image of the filter end face of the upper left cigarette [1]) when the cigarette [1] is at the predetermined proper location (location undisplaced). When the pattern image A1 does not coincide with the inspection image at the reference position, that is, when the pattern image A1 is displaced relative to the cigarette (the filter end face thereof), the pattern image A is shifted within the search area S. When the pattern image A1 and the inspection image (image of the end face of the cigarette) coincide with each other, a deviation amount (shift amount) $\Delta x$, $\Delta y$ by which the pattern image A1 is shifted from the comparison reference position is determined as a location in which the cigarette [1] exists within the inspection image.

The cigarette location ($\Delta x$, $\Delta y$) thus determined is given to an inspection area setting section 25. According to the cigarette location and the position of the search area S thus determined, the inspection area setting section 25 selectively cuts out from the inspection image memory 14 the image portion of the filter end face of the cigarette [1], which is determined with the determined positions located at the center, as a circular inspection area image D, for example, and provides the inspection area image D to an image inspection conducted by a contamination detection processing section (quality inspection means) 26.

Figure 6:
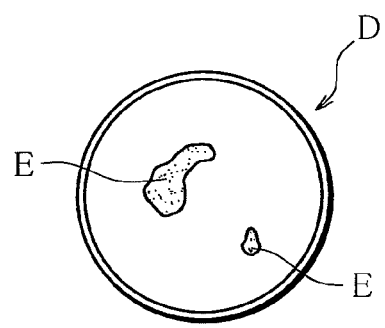
FIG. 6 shows an example of contaminations of a filter end face.

The contamination detection processing section 26, for example, subjects the inspection area image D to color filtering, to thereby detect a zone including a color component other than the color of the filter as a contaminated portion E, for example, as shown in FIG. 6. In the filtering, a color filter having a color component of the filters of the filter cigarettes is used to pick out an image zone having a color component other than the above color component. Particularly, the contamination detection processing section 26, for example, finds out the number of contaminated portions E detected in the inspection area image D, and finds out the area of the contaminated portions E, for example, as area percentage in the entire end face of the filter cigarette. The contamination detection processing of the filter end face of a cigarette is conducted when each of the cigarettes forming the cigarette bundle C is specified to find out the location of the cigarette according to the control parameter n, and the inspection area image D of the cigarette is selectively obtained on the basis of the result of the location detection.

The results of the contamination detection (the number of contaminations and the area percentage of contaminations), which are obtained with respect to each of the cigarettes forming the cigarette bundle C, are aggregated in a result aggregating section 27. For example, the total number of contaminations and the sum of the areas of contaminations in the entire cigarette bundle are obtained. However, when the size of contaminations is obtained as the area percentage, the average of area percentages of contaminated portions of cigarettes is obtained as the sum thereof.

With regard to the contamination inspection results aggregated as described, a result judging section (quality judging means) 28 discriminates the inspection results (the number and area of contaminations) obtained with respect to each of the cigarettes by using a predetermined threshold value, and judges the quality of each cigarette. The result judging section 28 also discriminates the aggregated values (the number and area of contaminations) of the inspection results obtained with respect to the cigarettes forming the cigarette bundle C in the foregoing manner by using a predetermined threshold value, and judges the quality thereof.

Specifically, for example, when contaminations exist in two or more spots in each cigarette or when the area percentage of contaminations exceeds 15 percent, the result judging section 28 determines that the cigarette bundle C includes a cigarette whose filter is considerably contaminated. When contaminations exist in fifteen or more spots in the cigarette bundle C or when the area percentage of contaminations exceeds 15 percent, the result judging section 28 determines that contaminations in filters are large in size even if contaminations in the filter end face of each cigarette are small.

When detecting the contaminations of the filters, the result judging section 28 gives a reject command to the wrapping machine to remove the cigarette bundle C contaminated in the filters from the wrapping process. Upon receipt of this reject command, the wrapping machine eliminates the cigarette bundle C from the closing turret 2, to thereby avoid the wrapping of the cigarette bundle C. This prevents the problem that the cigarette bundle C including a cigarette contaminated in the filter thereof is erroneously wrapped.

FIG. 7 shows a general routine (processing procedure) of the processing of inspecting the contaminations of filter end faces, which is performed by the image processor 20. The processing procedure will be briefly described below. First, the camera 10 is activated at the same time with the supply of the cigarette bundle C to the wrapping machine, and images the end face of the cigarette bundle C, thereby obtaining an inspection image <Step S1>. In order to analyze the inspection image and inspect contaminations of the filter end faces, the control parameter n is set at zero for initialization, and a below-mentioned inspection processing is started <Step S2>.

A judgment is made on whether the control parameter n reaches N indicative of the number of cigarettes forming the cigarette bundle C <Step S3>. If the control parameter n does riot reach [N], the control parameter n is incremented by one <Step S4>. According to the incremented control parameter n, the search area S for the inspection image is set <Step S5>. The pattern image A is then read in from the pattern image memory 15 <Step S6>. In the next step, pattern matching processing is sequentially carried out between the pattern image A and the inspection image B while shifting the pattern image A within the search area S <Step S7>. A position at which the pattern image A coincides with the inspection image is obtained as a deviation amount of the cigarette <Step S8>.

Thereafter, according to a cigarette location detected as the amount of deviation ($\Delta x$, $\Delta y$) from the proper location, the position of the image zone, which is obtained from the inspection image stored in the inspection image memory 14, is corrected, and only the image of the area of the filter end face of the cigarette is picked out as the inspection area image D <Step S9>. The inspection area image D undergoes the filtering, and thus, the presence or absence of contaminations, and further, the number and area of contaminations are obtained <Step S10>. These inspection results are temporarily stored so as to correspond to the control parameter n <Step S11>.

The routine returns to Step S3, and Steps S4 to S11 are repeatedly carried out until the control parameter n reaches N indicative of the number of cigarettes. When the control parameter n reaches N, this means that each of the N cigarettes forming the cigarette bundle C has been subjected the inspection of contaminations in the filter end face thereof. As mentioned, the inspection results of the cigarettes, which are stored correspondingly to the control parameter n, are aggregated <Step S12>. A comprehensive judgment is made as to the aggregation result and the inspection result with respect to each cigarette, and the cigarette bundle C including a cigarette contaminated in the filter or the cigarette bundle C in which the filter end faces are overall contaminated is judged as a defective product <Step S13>.

According to the cigarette inspection device for detecting contaminations in filter end faces, even if an array of the cigarette bundle C is disturbed, contaminations in filter end faces of cigarettes can be accurately detected in response to the disturbance of the array. Unlike conventional inspection devices, the cigarette inspection device of the present invention does not erroneously detect as a contamination a gap between cigarettes of the cigarette bundle C in which the array of the cigarettes is disturbed. The cigarette inspection device therefore does not cause the problem that the cigarette bundle C is rejected as a defective product when the array of cigarettes is just disturbed, and there is no problem in wrapping.

Since the filter end face of each of the cigarettes forming the cigarette bundle C is inspected, and the number and area of contaminations and the sum thereof are obtained to make a comprehensive judgment on the contaminations of filters, the cigarette inspection device is capable of detecting other defects than filter contaminations. More specifically, if the cigarettes forming the cigarette bundle C are less than the proper number, that is, if there is an omission of a cigarette (shortage), this abnormal can be detected because the filter end face cannot be detected at the corresponding position. If the orientation of the filter of a cigarette is reverse, it can be determined that there is an abnormal as the filter end face thereof is not detected in such a case. Alternatively, it is also possible to recognize a filter end face itself to be tobacco shreds that are detected as a contamination.

If a cigarette with a crushed filter is mixed in, the background portion on the inspection image, which is produced by the crushing of the filter, can be detected as a contamination. The abnormal can therefore be accurately detected. If particulates are attached all over the filter end face of the cigarette bundle C, it is possible Lo detect this as a contamination in consideration of the sum of the results of contamination inspection on each of the cigarettes.

According to the cigarette inspection device of the present invention, since the cigarette bundle C that has not yet been wrapped by the wrapping machine can be accurately eliminated from the wrapping process, it is possible to improve the product quality of a tobacco package obtained by wrapping the cigarette bundle C in the wrapping machine. The image processing can be easily performed by discrimination between filter end faces and the background thereof and by the color filtering applied to the inspection image of a filter end face, so that the processing thereof does not require much labor. Even if a takt time for the wrapping of the cigarette bundle C by using the wrapping machine is short, therefore, the present invention can sufficiently be applied.

The present invention is not limited to the foregoing embodiment. For example, in the embodiment, the cigarette bundle C is formed of twenty cigarettes, the number of cigarettes is not limited to any particular number. For example, the invention can be similarly applied to a cigarette bundle C including five or ten cigarettes. As to the camera 10 and the like, various types can be employed as well. The present invention may be modified in various ways without deviating from the gist thereof.

REFERENCE MARKS

10 Camera
13 Strobe
14 Inspection Image Memory
15 Pattern Image Memory
20 Image Processor
21 Parameter Controller
22 Search Area Setting Section
23 Matching Processing Section
24 Shift Processing Section
25 Inspection Area Setting Section
26 Contamination Detection Processing Section
27 Inspection Result Aggregating Section
28 Result Judging Section
A Pattern Image
B Inspection Image
C Cigarette Bundle
D Inspection Area Image
S Search Area

The invention claimed is:

1. A cigarette inspection device for imaging filter end faces in a cigarette bundle containing a predetermined number of filter cigarettes horizontally arranged when wrapping process of the cigarette bundle is unfinished, analyzing an inspection image in which the filter end faces are imaged, and inspecting quality of the filter end faces, comprising:

cigarette-location detecting means for determining a pattern image to be used for detecting a cigarette location on the basis of a preset location of each cigarette in the cigarette bundle, setting a search area with respect to each cigarette's location on the inspection image for detecting the cigarette location by the use of the pattern image, moving the pattern image obtained on the basis of cigarette location in the cigarette bundle within the search area that is determined with respect to each cigarette's location on the inspection image, and obtaining an image position at which the pattern image coincides with an image of the filter end face of the cigarette; and quality inspection means for cutting out an image of a filter end face of the cigarette from the inspection image according to the detected image position of the cigarette, and inspecting the quality of the filter end face of the cigarette.

2. The cigarette inspection device according to claim 1, wherein the pattern image is prepared as a partial image, in which a part of the filter end face of each of leftmost, rightmost, upper and lower cigarettes in the cigarette bundle is cut out in an arc-like shape against a background of an outer side of the cigarette bundle, and is then stored in a pattern image memory.

3. The cigarette inspection device according to claim 2, wherein the device further comprises quality judging means for aggregating results of contamination inspection, which are obtained with respect to cigarette locations in the cigarette bundle, and obtaining a result of contamination judgment on the cigarette bundle.

4. The cigarette inspection device according to claim 1, wherein said cigarette-location detecting means finds out a cigarette location in the inspection image as an amount of deviation ($\Delta x$, $\Delta y$) of the position of the pattern image from a reference location preset within the search area when the pattern image coincides with the image of the filter end face of the cigarette.

5. The cigarette inspection device according to claim 4, wherein the device further comprises quality judging means for aggregating results of contamination inspection, which are obtained with respect to cigarette locations in the cigarette bundle, and obtaining a result of contamination judgment on the cigarette bundle.

6. The cigarette inspection device according to claim 1, wherein said quality inspection means finds out a number of contaminations and/or area of contaminated regions in the filter end face.

7. The cigarette inspection device according to claim 6, wherein the device further comprises quality judging means for aggregating results of contamination inspection, which are obtained with respect to cigarette locations in the cigarette bundle, and obtaining a result of contamination judgment on the cigarette bundle.

8. The cigarette inspection device according to claim 1, wherein the inspection image is obtained by imaging the filter end faces in the cigarette bundle before a filter-side end of the cigarette bundle is closed with a wrapping material in a wrapping machine.

9. The cigarette inspection device according to claim 8, wherein the device further comprises quality judging means for aggregating results of contamination inspection, which are obtained with respect to cigarette locations in the cigarette bundle, and obtaining a result of contamination judgment on the cigarette bundle.

10. The cigarette inspection device according to claim 1, wherein the device further comprises quality judging means for aggregating results of contamination inspection, which are obtained with respect to cigarette locations in the cigarette bundle, and obtaining a result of contamination judgment on the cigarette bundle.

11. The cigarette inspection device according to claim 10, wherein said quality judging means judges that the cigarette bundle is defective when the number of contaminations or the area of contaminated regions in the filter end face exceeds a preset first threshold value or when the total number of contaminated regions or the total area of the contaminated regions in the filter end faces of cigarettes in the bundle exceeds a preset second threshold value.

* * * * *